United States Patent [19]
Toth et al.

[11] Patent Number: 4,605,785
[45] Date of Patent: Aug. 12, 1986

[54] 1,1-DIPHENYLPROPANOL DERIVATIVES, PROCESS FOR THEIR PREPARATION AND PHARMACEUTICAL COMPOSITIONS CONTAINING THEM

[75] Inventors: Edit Toth; Jozsef Torley; Eva Palosi; Szabolcs Szeberenyi; Laszlo Szporny; Sandor Gorog; Istvan Hajdu, all of Budapest, Hungary

[73] Assignee: Richter Gedeon Vegyeszeti Gyar RT, Budapest, Hungary

[21] Appl. No.: 565,838

[22] Filed: Dec. 27, 1983

[30] Foreign Application Priority Data

Dec. 28, 1982 [HU] Hungary ............................... 4181/82

[51] Int. Cl.$^4$ ............................................. C07C 43/20
[52] U.S. Cl. ..................... 568/649; 560/57; 564/323; 564/326; 562/468; 558/389
[58] Field of Search ............. 560/57; 568/649; 260/465 F; 564/323, 321; 562/468

[56] References Cited

U.S. PATENT DOCUMENTS

4,072,705  2/1978  Mieville .................................. 560/57
4,094,908  6/1978  Toth et al. ........................... 260/570

OTHER PUBLICATIONS

Chem. Abstracts 22, 410$^1$.
Chem. Abstracts 35, 1871$^2$.
Chem. Abstracts 40, 4712$^5$.
Chem. Abstracts 42, P 1015b.
Chem. Abstracts 47, 9548e.
Chem. Abstracts 50, 12390c.
Chem. Abstracts 50, 2509i.
Chem. Abstracts 55, 17915e.
Chem. Abstracts 55, 15413b.
Chem. Abstracts 75, P 103682b.
Chem. Abstracts 76, P 119921k.
Chem. Abstracts 82, 16477q.
Chem. Abstracts, 90, 86062q.
Chem. Abstracts 92, 52927b.

*Primary Examiner*—Paul J. Killos
*Attorney, Agent, or Firm*—Karl F. Ross; Herbert Dubno

[57] ABSTRACT

The invention relates to new 1,1-diphenylpropan-1-ol derivatives of the formula (I)

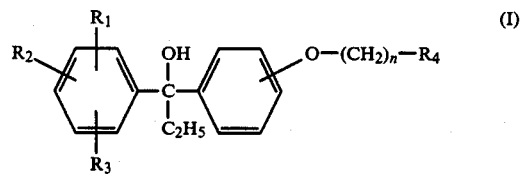

wherein
$R_1$ and $R_2$ independently represent hydrogen, halogen, trihalomethyl, alkyl having from one to 4 carbon atoms or alkoxy having from one to 4 carbon atoms,
$R_3$ is halogen, trihalomethyl, alkyl having from one to 5 carbon atoms or alkoxy having from one to 5 carbon atoms,
$R_4$ is phenyl optionally substituted by one or more identical or different substituents selected from the group of halogen, trihalomethyl, alkyl, alkoxy, cyano, nitro, amino, alkylamino, dialkylamino, hydroxyl, carboxyl or substituted carboxyl; dialkylaminocarbonyl or alkoxycarbonyl containing from one to 4 carbon atoms in the alkyl and alkoxy moieties, respectively,
n is 1, 2, 3, 4, or 5.

According to another aspect of the invention there are provided processes for the preparation of the compounds of formula (I).

The new compounds induce the polysubstrate monooxigenase enzyme system of liver and are devoid from other pharmacodinamic effects. Pharmaceutical compositions containing compounds of the formula (I) as active ingredient are also within the scope of the invention.

6 Claims, No Drawings

1,1-DIPHENYLPROPANOL DERIVATIVES, PROCESS FOR THEIR PREPARATION AND PHARMACEUTICAL COMPOSITIONS CONTAINING THEM

The invention relates to new 1,1-diphenylpropanol derivatives, to a process for their preparation and pharmaceutical compositions containing them as active ingredient. More particularly, the invention concerns new 1,1-diphenylpropan-1-ol derivatives of the formula (I)

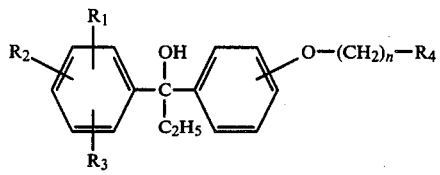

wherein
$R_1$ and $R_2$ independently represent hydrogen, halogen, trihalomethyl, alkyl having from one to 4 carbon atoms or alkoxy having from one to 4 carbon atoms,
$R_3$ is halogen, trihalomethyl, alkyl having from one to 4 carbon atoms or alkoxy having from one to 4 carbon atoms,
$R_4$ is phenyl optionally substituted by one or more identical or different substituents selected from the group of halogen, trihalomethyl, alkyl, alkoxy, cyano, nitro, amino, alkylamino, dialkylamino, hydroxyl, carboxyl or substituted carboxyl; dialkylaminocarbonyl or alkoxycarbonyl containing from one to 5 carbon atoms in the alkyl and alkoxy moieties, respectively,
n is 1, 2, 3, 4 or 5.

Compounds of similar structure are disclosed for example in the following publications: C.A. 22, 410[1]; 35, 1871[2]; 40, 4712[5]; 42, P 1015 b; 47, 9548 e; 50, 12390 c; 50, 2509 i; 55, 17915 e; 55, 15413 b; 75, P 103682 b; 76, P 119921 k; 82, 16477 g; 90, 86082 q; 92, 52927 b, without any mention of a pharmacological activity.

The new compounds of the formula (I) according to the invention may be prepared by the following processes:

(a) a propiophenone of the formula (II)

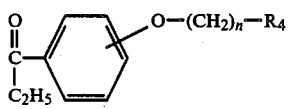

wherein n has the same meaning as defined above, and $R_4$ is a phenyl group optionally substituted as given hereinabove, is reacted with an organometallic compound of the formula (III)

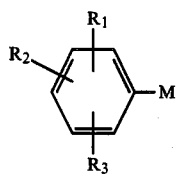

wherein $R_1$, $R_2$ and $R_3$ are the same as defined above, M is an alkali metal, preferably lithium, sodium or potassium or an MgX group, in which X stands for halogen; or (b) a benzophenone of the formula (IV)

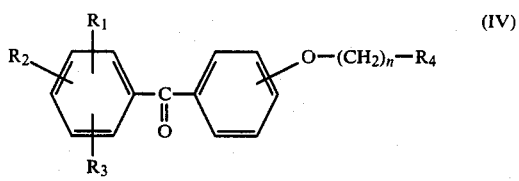

wherein $R_1$, $R_2$, $R_3$ and n are as defined above, and $R_4$ is a phenyl group optionally substituted as given hereinabove, is reacted with an organometallic compound containing an ethyl group, preferably ethyl magnesium halide or ethyl lithium; or (c) a propiophenone of the formula (V)

wherein $R_1$, $R_2$ and $R_3$ are as defined above, is reacted with a Grignard compound of the formula (VI)

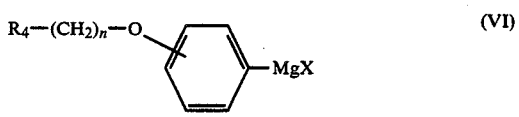

wherein n is as defined above, and $R_4$ is a phenyl group optionally substituted as given hereinabove,
X is halogen; or (d) a compound of the formula (VII)

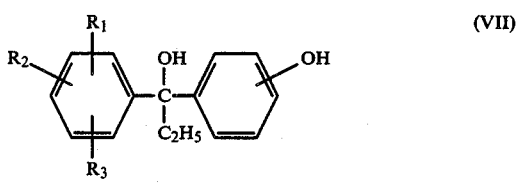

wherein $R_1$, $R_2$ and $R_3$ are as defined above, preferably in the form of an alkali metal or quaternary ammonium phenolate, is reacted with a compound of the formula (VIII)

wherein n and $R_4$ have the same meaning as defined above and
X represents an arylsulfonyloxy or alkylsulfonyloxy group or a halogen atom,
preferably in the presence of an acid binding agent; or (e) a compound of the formula (IX)

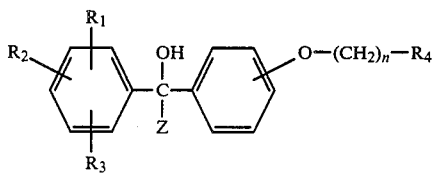

wherein $R_1$, $R_2$, $R_3$ and n are as defined above,
$R_4$ is a phenyl group optionally substituted as given hereinabove, and
Z is vinyl or ethinyl,
is reduced.

The starting compounds are known in the art or can be prepared by analogy with literature known methods.

The ketones of the formulae (II), (IV) and (V) may for example by synthetized by the well known Friedel-Crafts ketone synthesis (G. A. Olah: Friedel-Crafts and related reactions, III/1, Ed.; Interscience Publishers (1964), pp. 1–63).

The compounds of the formulae (III) and (VI) may for example be prepared by preparing a Grignard reactant from the corresponding substituted aryl halides in a known manner (M. S. Kharash et al.: Grignard reactions of nonmetallic substances, Ed., Prentice-Hall. Inc. (1954) pp. 5–90), while the preparation of alkali metal-organic compounds is for example described in Houben-Weyl: Methoden der Organischen Chemie, XIII/1, 134–159 and 389–405 (1970).

The compounds of the formula (VII) are for instance prepared by reacting the suitably substituted propiophenones with suitably substituted Grignard reactants (see e.g. M. S. Kharash et al.: Grignard reactions of nonmetallic substances, Ed., Prentice-Hall Inc. (1954) pp. 138–143).

Compounds of the formula (IX) in which Z represents a vinyl group can be prepared by reacting a benzophenone of the formula (IV) with vinyl-magnesium-halides, while if Z stands for an ethinyl group, compounds of the formula (IX) may be prepared by ethenylating a benzophenone of the formula (IV) e.g. as described in the Hungarian Patent Specification No. 166,769.

According to a preferred embodiment of process (a) provided by the invention a propiophenone of the formula (II) is reacted with an organometallic compound of the formula (III), preferably with a suitably substituted phenyl-magnesium chloride or bromide or phenyl lithium, in an anhydrous inert organic solvent. As a solvent preferably aprotic organic solvents, e.g. aliphatic ethers, such as diethyl ether, di-n-butyl ether, diethyleneglycol-dimethyl ether, alicyclic ethers, such as tetrahydrofurane, dioxane, aliphatic or aromatic hydrocarbons, such as ligroine, benzene, toluene, xylene, dimethyl sulfoxide, hexamethyl phosphorus amide or optional mixtures of the given solvents are employed.

The organometallic compounds are used in an at least equimolar amount. The reaction is preferably carried out in an inert gas atmosphere, e.g. nitrogen or argon atmosphere. The reaction temperature may be varied between $-60°$ C. and the boiling point of the solvent employed, and preferably is between $-30°$ C. and $100°$ C. After termination of the reaction the reaction mixture is decomposed, preferably with an aqueous ammonium chloride solution and the compound of the formula (I) formed is separated. If desired, the product can be purified by known techniques, e.g. distillation or crystallization.

According to process (b) a benzophenone of the formula (IV) is reacted with an at least equivalent amount of an ethyl-containing organometallic compound, preferably ethyl-magnesium bromide, iodide or ethyl lithium. The reaction is preferably performed in an anhydrous inert organic solvent, as described for process (c).

According to process (c) Grignard reactants of the formula (VI), preferably containing bromine in place of X, are reacted with propiophenones of the formula (V) in an at least equimolar amount, preferably in an anhydrous inert organic solvent, as described for process (a).

When carrying our process (d), preferably alkali metal or quaternary ammonium phenolates of the compounds of formula (VII) are condensed with mesylates, tosylates, bromides or more preferably, chlorides of the formula (VIII). The process is preferably performed in an inert solvent, in the presence of an acid binding agent, under anhydrous conditions or optionally in the presence of water and an organic solvent. As an organic solvent for example esters, such as ethyl acetate, ethers, such as dioxane, diethyl ether, tetrahydrofurane, hydrocarbons, e.g. benzene, toluene, xylene, ligroine, halogenated hydrocarbons, such as chloroform, chlorobenzene, acid amides, e.g. dimethyl formamide, ketones, such as methylethyl ketone, methylisobutyl ketone, acetone, alcohols, such as ethanol, propanol, etc. are employed.

The compounds of the formula (VII) are converted into the corresponding phenolates by methods known in the art, for example by reaction with alkali metal alcoholates, amides, hydrides, hydroxides, carbonates or quaternary ammonium compounds. As acid binding agents preferably inorganic or tertiary organic bases, e.g. sodium hydroxide, potassium hydroxide, potassium carbonate, triethyl amine, pyridine, etc. are employed. The reaction is optionally carried out in the presence of a catalyst, which preferably is an alkali metal halide, more preferably alkali metal iodide. The reaction temperature may be varied within wide limits, and preferably is between $20°$ C. and the boiling point of the solvent employed.

According to a preferred embodiment of process (e) the ethinyl or vinyl compounds of the formula (IX) are reduced by catalytic hydrogenation. As a catalyst metals, such as ruthenium, palladium, platinum, nickel, iron, copper, cobalt, chromium, zinc, molybdenum, tungsten, etc. or their oxides or sulfides may be used. The catalysts can for instance be prepared by reducing their stable oxides with hydrogen directly in the reaction vessel. This procedure is especially apt for the preparation of finely dispersed platinum or palladium catalysts. Catalytic hydrogenation may be accomplished also in the presence of catalysts precipitated on the surface of a carrier, e.g. charcoal, silica, alumina, alkali earth metal sulfates and carbonates. Raney nickel is also suitable for the reduction. The catalytic hydrogenation is preferably carried out in the presence of palladium, preferably palladium-on-charcoal or Raney nickel, in an organic solvent, inert under the reaction conditions. As solvents for example lower aliphatic alcohols, ethers, esters, aliphatic, cycloaliphatic or aromatic hydrocarbons or optional mixture thereof can be employed. Hydrogenation takes place under atmospheric or higher pressure, preferably not exceeding 506.6 kPa, at a temperature between $20°$ C. and the boiling temperature of the reaction mixture. It is preferred to work at room temperature and under atmospheric pressure until the hydrogen uptake terminates. The catalyst is then filtered off and the filtrate is evaporated. The product is purified for example by distillation or crystallization.

The compounds of the formula (I) provided by the invention effectively induce the polysubstrate monooxygenase enzyme system of the liver which plays an essential role in the regulation of metabolic processes, in the biotransformation of endogenic and exogenic substances. The compounds can therefore be used in a wide therapeutic field including enzymopatic icterus, Gilbert disease, neonatal hyperbilirubinemias, Cushing syndrome, Stein-Leventhal and Crigler-Najjar syndromes, tyreotoxic crises, intrahepatic cholestases, the treatment of nutritive allergies (to improve the efficiency of diagnostic methods, for example cholecystography). As an enzyme inducing compound generally phenobarbital is used in therapy, though it has undesirable CNS side effects (hypnotic, respiratory depressing effect) when employed in an effective dose. Therefore, there is a high demand for selective enzyme inducing compounds which are devoid of other pharmacodynamic activities.

The enzyme inducing activity was tested by the following methods: The change of hexabarbital oxidase activity was measured on Hann.-Wistar rats weighing 50–60 g. which were administered single 40 mg./kg. doses of the test compounds orally. One and 24 hours after treatment the animals were anaesthetized by a 60 mg./kg. i.v. dose of hexabarbital sodium, and the sleeping time, i.e. the time between the loss of righting reflex and full awakeness was measured (Noordhoex J.: Eur. J. Pharmacol., 3, 242, 1968). As a reference compound phenobarbital was used. The average of the groups and the standard error were determined. The results are given in Table 1, expressed in % of the control.

Abbreviations:
x̄=average value
S.E.=standard error of the average
n=number of animals The control group was treated with placebo.
Control=
39.0±6.02 (x̄±S.E.) minutes(1)
35.8±4.11 (x̄±S.E.) minutes(2)
A=1-(4-fluorophenyl)-1-(2-benzyloxyphenyl)-propane-1-ol
B=1-(2,5-dimethylphenyl)-1-(2-benzyloxyphenyl)-propane-1-ol
C=1-(3-trifluoromethylphenyl)-1-[4-(diethylcarbamoylmethoxy)-phenyl]-propane-1-ol
D=1-(3-chlorophenyl)-1-[2-(diethylcarbamoylmethoxy)-phenyl]-propane-1-ol
E=1-(3-chlorophenyl)-1-[2-(ethoxycarbonylmethoxy)-phenyl]propane-1-ol Table 1

| Compound (40 mg./kg.) | Hexabarbital sleeping time in %-age of the control | | n |
|---|---|---|---|
| | 1 h | 24 h | |
| A | 95 ± 20.2 | 46 ± 3.5 | 10 |
| B | 119 ± 7.7 | 58 ± 8.0 | 10 |
| C | 170 ± 10.0 | 44 ± 2.0 | 10 |
| D | 139 ± 14.4 | 50 ± 3.0 | 10 |
| E | 117 ± 1.1 | 58 ± 2.4 | 10 |
| phenobarbital | 250 ± 15.8 | 60 ± 7.3 | 10 |
| control | 100 ± 15.4(1) | 100 ± 11.5(2) | 10 |

The reason for shortening the narcosis time is that the treatment with the compounds provided by the invention accelerates the conversion of hexobarbital, which is a characteristic foreign body in the organism, into an inactive metabolite. The results set forth in Table 1 show that the activity of the compounds according to the invention in the hexobarbital oxidase in vivo activity test surpasses or is at least equal to the activity of phenobarbital. On the other hand, their great advantage is that they are devoid of inhibiting phases or at least the extent of inhibiting phase is essentially less than that of phenobarbital.

To evaluate the enzyme inducing activity of the compounds of formula (I) the activity of the polysubstrate monooxygenase enzyme system of the liver, after treatment with placebo and the test compounds, respectively, was also tested. Female Hann.-Wistar rats weighing 50–60 g. each were administered a single 40 mg/kg. dose of the test compounds orally. 24 hours after treatment the animals were decapitated and their livers were eliminated. After rinsing in an isotonic saline solution at 0° C., drying and weighing (at 0° C.) the livers were homogenized in a 0.1M Tris-HCl buffer (pH=7.4) containing 1.15% of potassium chloride at 0° C., centrifuged for 20 minutes at a speed of 9000 g, and the supernatant (postmitocondrial fraction) was used for the further tests. The microsoma fraction was prepared by the method of Cinti D. L. et al: Biochem. Pharmacol., 21, 3249 (1972). The cytochrome P-450 concentration was determined on the basis of the carbon monoxide differential spectrum of a reduced microsome suspension (Omura T. et al.: J. Biol. Chem. 239, 2370 (1964)). The quantity of cytochrome b-5 was determined from a NaDH differential spectrum (Raw J. et al.: J. Biol. Chem., 234, 1867 (1959)); the activity of NADPH: ferricytochrome C (P-450) reductase (E.C. 1.6.2.4) was measured by the method of Williams C. H. et al. (J. Biol. Chem., 237, 587 (1962)). The activity of the aniline hydroxylase from the velocity of the p-amino-phenol formation was determined by the method of R. S. et al.: Toxicol. Appl. Pharmacol., 22, 50 (1972), while the aminopyrine-demethylase activity was measured by the quantity of the formaldehyde formed, using the method developed by Gourlay G. K. et al.: Biochem. Pharmacol., 27, 965 (1978). The protein content was determined using the method by Lowry O. H. et al.: J. Biochem., 193, 265 (1951). The results are summarized in Table 2, expressed in % of the control. The control groups were treated with placebo.

TABLE 2

| | Control x̄ ± S.E. 100% ± S.E. % | Compound | |
|---|---|---|---|
| | | A | D |
| relative weight of liver g./100 g. of body weight | 4.3 ± 0.17 100 ± 3.9% | 109 ± 2.5% | 107 ± 4.4% |
| microsomal protein mg./g. of liver | 29.3 ± 1.01 100 ± 3.4% | 109 ± 3.8% | 120 ± 6.7% |
| cytochrome b-5 nmoles/g. of liver | 8.6 ± 0.43 100 ± 5.0% | 124 ± 3.8% | 122 ± 6.3% |
| cytochrome P-450 nmoles/g. of liver/min. | 12.8 ± 0.63 100 ± 4.9% | 170 ± 8.8% | 199 ± 17.7% |
| C(P-450) reductase nmoles/g. of liver/min. | 4868 ± 296.2 100 ± 6.1% | 155 ± 6.9% | 144 ± 11.9% |
| aniline hydroxylase nmoles/g. of liver/min. | 20.3 ± 0.88 100 ± 4.3% | 168 ± 8.9% | 189 ± 12.3% |
| aminopyrine demethylase nmoles/g. of | 254.8 ± 7.47 100 ± 2.9% | 150 ± 11.1% | 129 ± 6.0% |

TABLE 2-continued

| | Control x ± S.E. 100% ± S.E. % | Compound A | D |
|---|---|---|---|
| liver/min. | | | |

The results clearly show that the compounds essentially increase the quantity/activity of the components of the microsomal electron transport chain, and induce the enzyme system biotransforming the xenobiotics.

The acute toxicity of the compounds of formula (I) was determined on Hann.-Wistar rats selected from both sexes, weighing 160–180 g. each. The test compounds were administered in a single 500 mg./kg. oral dose. The animals were observed for 14 days. The results are set forth in the following Table 3, in which the percentage of the dead animals is indicated.

TABLE 3

| Compound (500 mg./kg.p.o.) | Dead animals (%) | n |
|---|---|---|
| A | φ | 10 |
| B | φ | 10 |
| C | φ | 10 |
| D | φ | 10 |
| E | φ | 10 |
| phenobarbital[x] | 100 | 10 |

[x]$LD_{50}$: 254 mg./kg.

As shown in the Table, the toxicity of the compounds of formula (I) is much lower than that of phenobarbital, therefore their therapeutic index is also much more favorable.

The CNS activity of the compounds of the general formula (I) was tested on mice, using the following test methods: electroshock (Swinyard, E. A., Brown, W. C., Goodman, L. S.: J. Pharmacol. Exp. Ther., 106, 319 1952), metrazole spasm (Everett, G. M., Richards, R. K.: J. Pharmacol. Exp. Ther., 81, 402, 1944), thiosemicarbazide spasm (Da Vanzo, J. P., Greig, M. E., Cormin, M. A.: Amer. J. Physiol., 201, 833, 1961), strichnine spasm (Kerley, T. L., Richards, A. G., Begley, R. W., Abreu, B. B., Wesver, L. C.: J. Pharmacol. Exp. Ther., 132, 360, 1961), nicotine spasm (Stone, C. A., Mecklenburg, K. L., Tornhans, M. L.: Arch. Int. Pharmacodyn., 117, 419, 1958), rotating rod (Kinnard, W. J., Carr, C. J.: J. Pharmacol. Exp. Ther.: 121, 354, 1957), protection of physostigmine lethality (Nose, T. and Kojima, M.: Europ. J. Pharmacol., 10, 83, 1970), yohimbine potentiating effect (Quinton, R. M.: Brit. J. Pharmacol., 21, 51, 1963), analgesic activity (Bianchi, C., Franceschini, J.: Brit. J. Pharm. Chemother., 9, 280, 1954).

The compounds of the formula (I) and phenobarbital were administered orally, in a dose of 40 mg./kg. and 80 mg./kg. The compounds provided by the invention proved ineffective, unlike phenobarbital, which has a significant anticonvulsive muscle coordinating and sedative effect already at a dose of 40 mg./kg. Accordingly, a further advantage of the instant compounds consists in the fact that they are devoid of CNS effects. Thus an important aspect of our invention is a pharmaceutical composition which comprises as active ingredient a pharmaceutically effective amount of a compound of formula (I) with at least one pharmaceutically inert carrier or diluent. Accordingly, the compounds provided by the invention can be transformed into conventional pharmaceutical compositions for oral, rectal and/or parenteral administration. For oral administration the compositions are formulated as tablets, dragées or capsules. As a vehicle for example lactose or starch is employed, while typical excipients and granulation aids include gelatin, carboxymethylcellulose sodium, methylcellulose, polyvinylpyrrolidone and starch gum. As a disintegrating substance for example potato starch of microcrystalline cellulose are added to the oral formulations but ultraamylopectine or formaldehyde-casein, etc. may equally be employed. As antiadhesives and gliding substances e.g. talc, colloidal silica, stearin, calcium and magnesium stearate, etc. is used.

The tablets are prepared for example by wet granulation and subsequent pressing. The active ingredients, vehicles and optionally a portion of the disintegrating substances are admixed and the mixture is granulated with an aqueous, alcoholic or aqueous-alcoholic solution of the excipients in suitable equipment, and the granulate is dried. The dry granulate is supplemented with the remaining disintegrating substance, the gliding substances and antiadhesives and the mixture is pressed into tablets. If desired, the tablets are supplied with a dividing groove to assist administration. The tablets may be prepared from a mixture of the active ingredients and suitable additives also by direct pressing.

If desired, the tablets may be coated, using protecting, flavouring or coloring substances conventionally used in the preparation of pharmaceutical compositions, e.g. sugar, cellulose derivatives (methyl- or ethylcellulose, carboxymethylcellulose sodium, etc.), polyvinylpyrrolidone, calcium phosphate, calcium carbonate, food pigments, food enamels, aroma substances, iron oxide pigments, etc.

Capsules are prepared by filling a mixture of the active ingredients and additives into suitable capsules.

For rectal administration suppositories are prepared. In addition to the active ingredient the suppositories contain a carrier mass, i.e. adeps pro suppository. As a carrier vegetable fats, for example hardened vegetable oils, triglycerides of fatty acids containing 12 to 18 carbon atoms, preferably a preparate marketed under the registered trade name Witepsol are employed. The active ingredient is homogeneously distributed in the melted carrier mass and suppositories are casted.

For parenteral administration the pharmaceutical compositions are formulated as injection preparates. Injection solutions are prepared by dissolving the active ingredients in distilled water and/or various organic solvents, such as glycol ethers, optionally in the presence of dissolution mediators, e.g. polyoxyethylenesorbitanemonolaurate, monooleate or monostearate (Tween 20, Tween 60, Tween 80). The injection solutions may contain also various additives, such as preservatives, e.g. benzyl alcohol, p-oxy-benzoic acid methyl or propyl ester, benzalkonium chloride or phenylmercuri borate, etc., antioxidants, e.g. ascorbic acid, tocopherol, sodium pyrosulfate and optionally complexing agents to bind metal traces, e.g. ethylenediamine tetraacetate, buffers to adjust the pH and local anaesthetics, e.g. lidocaine. The injection preparates are filtered, filled into ampoules and sterilized.

The daily doses are between 1.0 and 200.0 mg./kg., preferably 5.0 and 50.0 mg./kg., depending on the state of the patient. Preferably more smaller doses are administered in a day.

Of the compounds having the formula (I) the following representatives are considered particularly important:

1-(3-trifluoromethyl-phenyl)-1-(4-benzyloxyphenyloxyphenyl)-propan-1-ol;
1-(4-fluorophenyl)-1-(4-benzyloxyphenyl)-propan-1-ol;
1-(2,5-dimethylphenyl)-1-(2-benzyloxyphenyl)-propan-1-ol;
1-(2-methoxyphenyl)-1-[4-(3-phenylpropoxy)-phenyl]-propan-1-ol;
1-(2,4-dichlorophenyl)-1-(4-benzyloxyphenyl)-propan-1-ol;
1-(2-trifluoromethylphenyl)-1-(4-benzyloxyphenyl)-propan-1-ol;
1-(4-bromophenyl)-1-(4-benzyloxyphenyl)-propan-1-ol;
1-(4-trifluoromethylphenyl)-1-(4-benzyloxyphenyl)-propan-1-ol;
1-(2-methoxyphenyl)-1-(4-benzyloxyphenyl)-propan-1-ol;
1-(3-trifluoromethylphenyl)-1-[4-(diethylcarbamoylmethoxy)-phenyl]-propan-1-ol;
1-(3-chlorophenyl)-1-[2-(ethoxycarbonylmethoxy)-phenyl]-propan-1-ol;
1-(3-chlorophenyl)-1-[2-(diethylcarbamoylmethoxy)-phenyl-]propan-1-ol;
1-(3-trifluoromethyl)-1-[4-(3-ethoxycarbonylpropoxy)-phenyl]-propan-1-ol;
1-(3-chlorophenyl)-1-[4-(ethoxycarbonylmethoxy)-phenyl]-propan-1-ol;
1-(3-trifluoromethylphenyl)-1-[4-(ethoxycarbonylmethoxy)-phenyl]-propan-1-ol;
1-(2,5-dimethylphenyl)-1-[2-(diethylcarbamoylmethoxy)-phenyl]-propan-1-ol;
1-(3-chlorophenyl)-1-[4-(diethylcarbamoylmethoxy)-phenyl]-propan-1-ol;
1-(4-fluorophenyl)-1-[4-(diethylcarbamoylmethoxy)-phenyl]-propan-1-ol;
1-(2-trifluoromethylphenyl)-1-[4-(diethylcarbamoylmethoxy)-phenyl]-propan-1-ol.

The invention will now be illustrated in greater detail in the following specific Examples, which are given for illustration and not limitation of our invention.

EXAMPLE 1

1-(3-Trifluoromethylphenyl)-1-(4-benzyloxyphenyl)-propan-1-ol

To a Grignard reactant prepared from 1.46 g. of magnesium turnings and 13.5 g. of 3-trifluoromethyl-bromobenzene in 34 ml. of dry tetrahydrofurane a solution of 9.61 g. of 4-benzyloxy-propiophenone in 50 ml. of dry tetrahydrofurane is added dropwise, under moderate reflux. The reaction mixture is slightly boiled for a further hour. The progress of the reaction can be monitored by thin layer chromatography. After termination of the reaction the reaction mixture is cooled and poured onto a mixture of glacial acetic acid and ice. The solvent phase is washed with a saturated aqueous sodium chloride solution and dried over anhydrous magnesium sulfate. The solvent is distilled off in vacuo. 15 g. of the named compound are obtained, which can be recrystallized from n-heptane. Melting point: 50°–51° C.

Analysis for $C_{23}H_{21}F_3O_2$: Calculated: C 71.49%, H 5.84%, F 14.75%; Found: C 71.60%, H 5.39%, F 14.88%.

EXAMPLE 2

1-(4-Fluorophenyl)-1-(4-benzyloxyphenyl)-propan-1-ol

To 125 ml. of a 0.8 molar ethereal ethyl lithium solution a solution of 12.25 g. of 4-fluoro-4'-benzyloxy-benzophenone in 180 ml. of dry ether is added dropwise, in argon atmosphere, with stirring at −20° C. The reaction mixture is allowed to warm up to room temperature and stirred for further 90 minutes. It is then poured into saturated aqueous ammonium chloride solution under cooling. The aqueous phase is extracted with ether, the organic phases are combined and washed to neutral with water. After drying over anhydrous magnesium sulfate ether is distilled off under reduced pressure. The solid residue is crystallized from a mixture of ethyl acetate and n-heptane to yield 7.4 g. of the named compound, melting at 56°–57° C.

Analysis for $C_{22}H_{21}FO_2$: Calculated: C 78.75%, H 6.29%, F 5.65%; Found: C 78.31%, H 6.40%, F 5.78%.

EXAMPLE 3

1-(3-Chlorophenyl)-1-(4-benzyloxyphenyl)-propan-1-ol

To a Grignard reactant prepared from 7.2 g. of magnesium turnings and 32.6 g. of ethyl bromide in 120 ml. of dry ether a solution of 24 g. of 3-chloro-4'-benzyloxy-benzophenone in 120 ml. of tetrahydrofurane is added dropwise, with stirring at 0° to 5° C. The reaction mixture is then slightly boiled for 30 minutes, and the Grignard complex is decomposed with a saturated aqueous solution of ammonium chloride under cooling. The aqueous phase is extracted with ether, the combined organic phases are washed with saturated aqueous sodium chloride solution. After drying over anhydrous sodium sulfate, the solvent is distilled off under reduced pressure. Crystallization of the residue from a mixture of ethyl acetate and n-hexane yields 16.2 g. of the named compound, melting at 52°–53° C.

Analysis for $C_{22}H_{21}ClO_2$: Calculated: C 74.88%, H 6.00%, Cl 10.05%; Found: C 75.11%, H 5.88%, Cl 10.15%.

EXAMPLE 4

1-(2,5-Dimethylphenyl)-1-(2-benzyloxyphenyl)-propan-1-ol

To 100 ml. of a 1.5 molar solution of 2-benzyloxyphenyl magnesium bromide in tetrahydrofurane a solution of 24.3 g. of 2',5'-dimethyl-propiophenone in 50 ml. of dry tetrahydrofurane is added under moderate reflux. The reaction mixture is stirred under slight boiling for 30 minutes, cooled and poured onto a saturated solution of ammonium chloride in ice water. Tetrahydrofurane is distilled off under reduced pressure, and the residue is extracted with benzene. The benzene phase is washed to neutral with water, and dried over anhydrous sodium sulfate. The benzene is evaporated in vacuo and the residue is fractionated to yield 43.9 g. of the named compound, boiling at 160°–162° C./1.33 Pa.

Analysis for $C_{24}H_{26}O_2$: Calculated: C 83.20%, H 7.56%; Found: C 83.42%, H 7.60%.

EXAMPLE 5

1-(2-Methoxyphenyl)-1-[4-(3-phenylpropoxy)-phenyl]-propan-1-ol 6.45 g. of 1-(2-methoxyphenyl)-1-(4-hydroxyphenyl)-propan-1-ol, 5.5 g. of 3-phenylpropyl bromide, 6.5 g. of anhydrous potassium carbonate, 0.5 g. of potassium iodide and 65 ml. of dry acetone are slightly boiled for 15 hours, with stirring. After cooling, acetone is distilled off under reduced pressure, to the residue water is added and it is extracted with benzene. The organic phase is washed to neutral with water, a 5% aqueous sodium hydroxide solution and again water. After drying over anhydrous magnesium sulfate the solution is evaporated in vacuo. The residue is crystallized from n-hexane to yield 7.8 g. of the named compound, melting at 75°–76° C.

Analysis for $C_{25}H_{23}O_3$: Calculated: C 79.75%, H 7.50%; Found: C 79.80%, H 7.63%.

EXAMPLE 6

1-(2,4-Dichlorophenyl)-1-(4-benzyloxyphenyl)-propan-1-ol 11.5 g. of 1-(2,4-dichlorophenyl)-1-(4-benzyloxyphenyl)-propargyl alcohol are dissolved in 115 ml. of dry benzene, and the reaction mixture is hydrogenated in the presence of 0.6 g. of a 10% palladium-on-charcoal catalyst until the uptake of the calculated amount of hydrogen is complete. Thereafter the catalyst is filtered off, and the solvent is evaporated under reduced pressure. Crystallization of the residue from n-pentane yields 7.9 g. of the named compound, melting at 56°–57° C.

Analysis for $C_{22}H_{20}Cl_2O_2$: Calculated: C 68.22%, H 5.20%, Cl 18.31%; Found: C 68.35%, H 5.23%, Cl 18.50%.

EXAMPLE 7

1-(2,5-Dimethylphenyl)-1-(4-benzyloxyphenyl)-propan-1-ol 10.3 g. of 1-(2,5-dimethylphenyl)-1-(4-benzyloxyphenyl)-allyl alcohol are dissolved in 110 ml. of ethanol and the reaction mixture is hydrogenated under atmospheric pressure, in the presence of 3.5 g. of Raney nickel catalyst. After uptake of the calculated amount of hydrogen is complete, the catalyst is filtered off. Ethanol is distilled off under reduced pressure. As a residue 9 g. of the named compound are obtained as a viscous oil, boiling at 190°–192° C./26.6 Pa.

Analysis for $C_{24}H_{26}O_2$: Calculated: C 83.20%, H 7.56%; Found: C 83.28%, H 7.44%.

EXAMPLE 8

1-(4-Fluorophenyl)-1-(4-benzyloxyphenyl)-propan-1-ol

To a Grignard reactant prepared from 14.5 g. of magnesium turnings and 104.3 g. of 4-fluorobromobenzene in 200 ml. of dry ether a solution of 120.1 g. of 2'-benzyloxypropiophenone in 200 ml. of ether is added dropwise, at −5° C. The reaction mixture is then slightly boiled for one hour, whereupon it is decomposed with a 10% aqueous ammonium chloride solution, under cooling. The ethereal phase is washed to neutral with water and dried over anhydrous magnesium sulfate. The solvent is distilled off under reduced pressure and the residue is crystallized from n-hexane. 124.3 g. of the named compound are obtained, melting at 64°–65° C.

Analysis for $C_{22}H_{21}FO_2$: Calculated: C 78.55%, H 6.29%, F 5.65%; Found: C 78.69%, H 6.22%, F 5.87%.

Starting from the corresponding starting materials the following compounds can be prepared on the analogy of Examples 1 to 8.

1-(2-Trifluoromethylphenyl)-1-(4-benzyloxyphenyl)-propan-1-ol, melting point: 77°–78° C.

Analysis for $C_{23}H_{21}F_3O_2$: Calculated: C 71.49%, H 5.48%, F 14.75%; Found: C 71.65%, H 5.57%, F 14.66%.

1-(4-Bromophenyl)-1-(4-benzyloxyphenyl)-propan-1-ol, melting point: 86°–87° C.

Analysis for $C_{22}H_{21}BrO_2$: Calculated: C 66.50%, H 5.33%, Br 20.12%; Found: C 66.38%, H 5.15%, Br 20.33%.

1-(4-Trifluoromethylphenyl)-1-(4-benzyloxyphenyl)-propan-1-ol, melting point: 79°–80° C.

Analysis for $C_{23}H_{21}F_3O_2$: Calculated: C 71.49%, H 5.48%, F 14.75%; Found: C 71.60%, H 5.62%, F 14.58%.

1-(2-Methoxyphenyl)-1-(4-benzyloxyphenyl)-propan-1-ol, melting point: 92°–93° C.

Analysis for $C_{23}H_{24}O_3$: Calculated: C 79.28%, H 6.94%; Found: C 79.50%, H 6.97%.

EXAMPLE 9

1-(3-Trifluoromethylphenyl)-1-[4-(diethylcarbamoylmethoxy)-phenyl]-propan-1-ol 14.8 g. 1-(3-trifluoromethylphenyl)-1-(4-hydroxyphenyl)-propan-1-ol, 7.6 g. of anhydrous potassium carbonate, 2 g. of potassium iodide, 8.2 g. of monochloroacetic acid diethylamide and 150 ml. of dry acetone are boiled for 5 hours, under stirring. The reaction mixture is cooled and the solvent is distilled off under reduced pressure. To the residue water is added and it is extracted with benzene. The benzene phase is shaken with water and subsequently a 5% aqueous sodium hydroxide solution and washed to neutral with water. It is dried over anhydrous sodium sulfate, filtered off and the solution is evaporated in vacuo. The solid residue is crystallized from a mixture of n-hexane and ethyl acetate. 17.6 g. of the named compound are obtained, melting at 83°–84° C.

Analysis for $C_{22}H_{26}F_3NO_3$: Calculated: C 64.53%, H 6.40%, N 3.42%, F 13.92%; Found: C 64.29%, H 6.44%, N 3.28%, F 13.75%.

EXAMPLE 10

1-(3-Chlorophenyl)-1-[2-(ethoxycarbonylmethoxy)-phenyl]-propan-1-ol

A solution of 5.3 g. of 1-(3-chlorophenyl)-1-(2-hydroxyphenyl)-propan-1-ol and 3.8 g. of monobromoacetic acid ethyl ester in 60 ml. of dry acetone is boiled in the presence of 0.8 g. of potassium iodide and 6 g. of anhydrous potassium carbonate for 5 hours, with stirring. After cooling the reaction mixture solvent is distilled off under reduced pressure, to the residue water is added and it is extracted with benzene. The benzene phase is extracted with water and a 5% aqueous sodium hydroxide solution, washed to neutral with water and dried over anhydrous magnesium sulfate. Benzene is then distilled off in vacuo and the residue is crystallized from n-hexane. 5.6 g. of the named compound are obtained, melting at 83°–84° C.

Analysis for $C_{19}H_{21}ClO_4$: Calculated: C 65.42%, H 6.07%, Cl 10.16%; Found: C 65.60%, H 6.15%, Cl 10.38%.

EXAMPLE 11

1-(3-Chlorophenyl)-1-[2-(diethylcarbamoylmethoxy)-phenyl]-propan-1-ol 5.3 g. of 1-(3-chlorophenyl)-1-(2-hydroxyphenyl)-propan-1-ol and 3.3 g. of monochloroacetic acid diethyl amide are dissolved in 36 ml. of n-propanol, and the reaction mixture is boiled for 4 hours, with stirring in the presence of 3 g. of anhydrous potassium carbonate. After cooling the solvent is distilled off under reduced pressure. To the residue water is added and it is extracted with ether. The ethereal solution is washed with water, a 5% aqueous sodium hydroxide solution and again with water until neutral. After drying over anhydrous magnesium sulfate, the solvent is distilled off in vacuo. The residue is crystallized from a mixture of n-hexane and ethyl acetate to yield 5.8 g. of the named compound, melting at 93°–94° C.

Analysis for $C_{21}H_{26}ClNO_3$: Calculated: C 67.10%, H 6.97%, N 3.73%, Cl 9.43%; Found: C 67.25%, H 7.11%, N 4.00%, Cl 9.57%.

EXAMPLE 12

1-(3-Trifluoromethylphenyl)-1-[4-(3-ethoxycarbonyl-propoxy)-phenyl]-propan-1-ol A solution of 29.6 g. of 1-(3-trifluoromethylphenyl)-1-(4-hydroxyphenyl)-propan-1-ol and 21.5 g. of 4-bromobutyric acid ethylester in 200 ml. of ethyl acetate is boiled for 15 hours in the presence of 0.7 g. of tetrabutylammonium hydrogensulfate and 30.5 g. of dry potassium carbonate, with stirring. After cooling down the reaction mixture, the solvent is distilled off in vacuo. To the residue water is added, and it is extracted with benzene. The organic phase is shaken with water, a 5% aqueous potassium hydroxide solution and washed to neutral with water. After drying over anhydrous sodium sulfate benzene is distilled of in vacuo. Fractionation of the residue affords 30.8 g. of the named compound, boiling at 168°–170° C./1.33 Pa.

Analysis for $C_{22}H_{25}F_3O_4$: Calculated: C 64.38%, H 6.14%, F 13.89%; Found: C 64.60%, H 6.20%, F 13.75%.

Starting from suitable starting materials the following compounds can be prepared on the analogy of Examples 9 to 12.

1-(3-chlorophenyl)-1-[4-(ethoxycarbonylmethoxy)-phenyl]-propan-1-ol, boiling point: 176°–178° C./1.33 Pa.

Analysis for $C_{19}H_{21}ClO_4$: Calculated: C 65.42%, H 6.07%, Cl 10.16%; Found: C 65.57%, H 6.28%, Cl 10.28%.

1-(3-Trifluoromethylphenyl)-1-[4-(ethoxycarbonylmethoxy)phenyl]-propan-1-ol, melting point: 61°–62° C.

Analysis for $C_{20}H_{21}F_3O_4$: Calculated: C 62.82%, H 5.53%, F 14.91%; Found: C 62.95%, H 5.48%, F 15.20%.

1-(2,5-Dimethylphenyl)-1-[2-(diethylcarbamoylmethoxy)-phenyl]-propan-1-ol, melting point: 78.5°–79.5° C.

Analysis for $C_{23}H_{31}NO_3$: Calculated: C 74.76%, H 8.46%, N 3.79%; Found: C 74.80%, H 8.61%, N 3.90%.

1-(3-Chlorophenyl)-1-[4-(diethylcarbamoylmethoxy)-phenyl]-propan-1-ol, melting point: 97°–98° C.

Analysis for $C_{21}H_{26}ClNO_3$: Calculated: C 67.10%, H 6.97%, N 3.73%, Cl 9.43%. Found: C 67.22%, H 7.11%, N 3.54%, Cl 9.67%.

1-(4-Fluorophenyl)-1-[4-(diethylcarbamoylmethoxy)-phenyl]-propan-1-ol, boiling point: 198°–201° C./1.33 Pa.

Analysis for $C_{21}H_{26}FNO_3$: Calculated: C 70.17%, H 7.29%, N 3.90%, F 5.29%; Found: C 70.32%, H 7.50%, N 4.11%, F 5.38%.

1-(2-Trifluoromethylphenyl)-1-[4-/diethylcarbamoylmethoxy)-phenyl]-propan-1-ol, boiling point: 185°–187° C./1.33 Pa.

Analysis for $C_{22}H_{26}F_3NO_3$: Calculated: C 64.53%, H 6.40%, N 3.42%, F 13.92%; Found: C 64.50%, H 6.54%, N 3.64%, F 14.18%.

EXAMPLE 13

This example illustrates the preparation of pharmaceutical compositions containing new compounds according to the invention as active ingredient.

Tablets

Composition of a single tablet:

| | |
|---|---|
| active ingredient | 100.0 mg. |
| lactose | 184.0 mg. |
| potato starch | 80.0 mg. |
| polyvinylpyrrolidone | 8.0 mg. |
| talc | 12.0 mg. |
| magnesium stearate | 2.0 mg. |
| aerosil (colloidal silica) | 2.0 mg. |
| ultraamylopectin | 12.0 mg. |

From the above ingredients 400-mg. tablets are prepared by wet granulation and pressing.

Active ingredient: 1-(3-chlorophenyl)-1-8.2-(ethoxycarbonylmethoxy)-phenyl]-propan-1-ol.

Dragées

Tablets prepared as described above are coated with a layer consisting of sugar and talc, in a known manner. Dragées are polished with a mixture of bee wax and carnauba wax. Weight of a dragée: 500.0 mg.

Capsules

Composition of a single capsule:

| | |
|---|---|
| active ingredient | 50.0 mg. |
| lactose | 100.0 mg. |
| potato starch | 30.0 mg. |
| talc | 2.0 mg. |
| cellulose (microcrystalline) | 8.0 mg. |

The active ingredient is thoroughly admixed with the additives and the mixture is passed through a 0.32 mm. screen and filled into hard gelatine capsules of size 4.

Active ingredient: 1-(4-fluorophenyl)-1-(2-benzyloxyphenyl)-propan-1-ol.

Suppositories

Composition of a suppository:

| | |
|---|---|
| active ingredient | 100.0 mg. |
| lactose | 200.0 mg. |
| basic substance of suppository (e.g. Witepsol H) | 1700.0 mg. |

The basic material is melted and then cooled to 35° C. The active ingredient is thoroughly blended with the lactose, and the mixture is homogenized in the basic substance in a homogenizer. The obtained mass is filled into cooled molds. One suppository weighs 2000 mg.
Active ingredient: 1-(2,5-dimethylphenyl)-1-(2-benzyloxyphenyl)-propan-1-ol.

Suspensions

Composition of 100 ml. of a suspension:

| active ingredient | 1.00 g. |
|---|---|
| sodium hydroxide | 0.26 g. |
| citric acid | 0.30 g. |
| nipagin (4-hydroxybenzoic acid methyl ester sodium salt) | 0.10 g. |
| carbopol (polyacrylic acid) | 0.30 g. |
| ethanol (96%) | 1.00 g. |
| raspberry aroma | 0.60 g. |
| sorbite (70% aqueous solution) | 71.00 g. |
| distilled water | ad 100.00 ml. |

To a solution of nipagin and citric acid in 20 ml. of distilled water carbopol is added in small portions, with vigorous stirring and the solution is allowed to stand for 10 to 12 hours. Thereafter a solution of the above amount of sodium hydroxide in 1 ml. of water, an aqueous solution of sorbite and finally the ethanolic solution of raspberry aroma are added dropwise, with stirring. After adding the active ingredient in small portions the mixture is suspended by a homogenizer. The suspension is then made up to 100 ml. with distilled water and the syrup obtained is passed through a colloid mill.
Active ingredient: 1-(3-chlorophenyl)-1-[2-(diethylcarbamoylmethoxy)-phenyl]-propan-1-ol.

We claim:

1. A compound of the Formula (I)

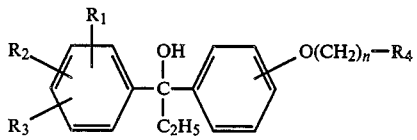

wherein
$R_1$ and $R_2$ independently represent hydrogen, halogen, trihalomethyl, $C_1-C_4$ alkyl or $C_1-C_4$ alkoxy;
$R_3$ is halogen, trihalomethyl, $C_1-C_4$ alkyl, or $C_1-C_4$ alkoxy;
$R_4$ is phenyl which can be substituted by one or more identical or different substituents selected from the group consisting of halogen, trihalomethyl, alkyl, alkoxy, cyano, nitro, amino, alkylamino, dialkylamino, hydroxyl, carboxyl, and substituted carboxyl; and
n is 1, 2, 3, 4 or 5.

2. The compound of the Formula (I) defined in claim 1 which is:

1-(4-fluorophenyl)-1-(4-benzyloxyphenyl)-propan-1-ol; or
1-(2,5-dimethylphenyl)-1-(2-benzyloxyphenyl)-propan-1-ol.

3. A process for the preparation of a compound of the Formula (I)

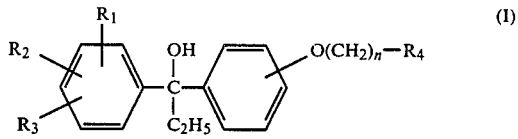

wherein
$R_1$ and $R_2$ independently represent hydrogen, halogen, trihalomethyl, $C_1-C_4$ alkyl, or $C_1-C_4$ alkoxy;
$R_3$ is halogen, trihalomethyl, $C_1-C_4$ alkyl or $C_1-C_4$ alkoxy;
$R_4$ is phenyl which can be substituted by one or more identical or different substituents selected from the group consisting of halogen, trihalomethyl, alkyl, alkoxy, cyano, nitro, amino, alkylamino, dialkylamino, hydroxyl, carboxyl, and substituted carboxyl; and
n is 1, 2, 3, 4 or 5
which comprises the step of:
reacting a compound of the Formula (II)

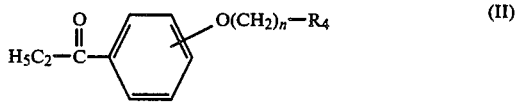

with a compound of the Formula (III)

wherein M is an alkali metal or an MgX group and X is halogen, in an anhydrous inert organic solvent at a temperature between −60° C. and the boiling point of the solvent wherein the compound of the Formula (III) is present in an amount at least equimolar to that of the compound of the Formula (II).

4. The process defined in claim 3 wherein the reaction is carried out at a temperature of −30° C. to 100° C.

5. The process defined in claim 3 wherein the inert organic solvent is an aprotic organic solvent.

6. The process defined in claim 3 wherein the reaction is carried out in an inert atmosphere.

* * * * *